United States Patent [19]

Gastaud

[11] Patent Number: 5,399,590
[45] Date of Patent: Mar. 21, 1995

[54] QUATERNARY AMMONIUM SALTS AND PHARMACEUTICAL COMPOSITIONS CONTAINING THEM

[76] Inventor: Jean M. Gastaud, Domaine Bellecombe, 74930 Reignier, France

[21] Appl. No.: 969,832

[22] PCT Filed: Apr. 10, 1992

[86] PCT No.: PCT/FR92/00317
§ 371 Date: Jan. 14, 1993
§ 102(e) Date: Jan. 14, 1993

[87] PCT Pub. No.: WO92/20646
PCT Pub. Date: Nov. 26, 1992

[30] Foreign Application Priority Data

May 10, 1991 [FR] France ................... 91 05693

[51] Int. Cl.$^6$ ............... A61K 31/14; C07C 211/63
[52] U.S. Cl. ................... 514/643; 514/478; 514/512; 514/534; 514/546; 514/557; 514/626; 558/276; 560/110; 560/168; 560/250; 562/574; 564/197; 564/291; 564/292
[58] Field of Search ............. 564/197, 291, 292; 562/574; 560/110, 169, 250; 558/276; 514/478, 512, 534, 546, 557, 626, 642

[56] References Cited

U.S. PATENT DOCUMENTS

| | | | |
|---|---|---|---|
| 3,420,822 | 1/1969 | Casadio | 260/240 |
| 3,932,664 | 1/1976 | Strycker | 424/330 |
| 4,444,971 | 4/1984 | McEntire | 526/292.2 |
| 4,710,304 | 12/1987 | Lang | 210/734 |
| 4,824,867 | 4/1989 | Smith et al. | 514/642 |
| 5,030,756 | 7/1991 | Deppert et al. | 564/291 |

FOREIGN PATENT DOCUMENTS 519324 2/1931 Germany .

OTHER PUBLICATIONS

Almarzoqi et al., Tetrahedron, vol. 42, No. 2 (1980) pp. 601–607.
Bridges et al., Chemical Abstracts, vol. 73 (1970) 11756j.
Mistry et al., Chemical Abstracts, vol. 115 (1991) 49218j.
Norholm et al., Chemical Abstracts, vol. 96 (1982) 19764f.
Chiou, Chemical Abstracts, vol. 78 (1973) 52537k.
8th Collective Index, Chemical Abstracts (1967) p. 21655, vol. 3, lines 87–89; p. 21005, col. 2, lines 45–47.

*Primary Examiner*—Richard L. Raymond
*Attorney, Agent, or Firm*—Bierman and Muserlian

[57] ABSTRACT

The invention relates to the field of organic chemistry and more particularly to that of therapeutic chemistry.
More particularly it relates to new quaternary ammonium salts of general formula (I):

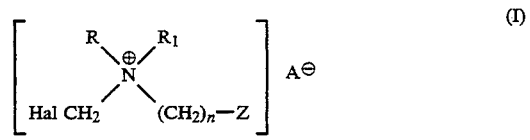

in which Hal is a halogen atom other than fluorine R and $R_1$, identical or different, are lower alkyl radicals, n is an integer varying from 2 to 16, Z is an alkenyl radical having up to 3 carbon atoms, a carboxyl, or the $OR_2$ group in which $R_2$ is a hydrogen, a lower alkyl radical, an acyl remainder, a tocol radical, a sterol radical or a carboxamide chain and A is a hydroxyl or an anion of a mineral or organic acid.

The compounds according to the invention are the active ingredients of pharmaceutical compositions with an anti-tumorous and/or immuno-suppressive action.

3 Claims, No Drawings

QUATERNARY AMMONIUM SALTS AND PHARMACEUTICAL COMPOSITIONS CONTAINING THEM

The present invention relates to the field of organic chemistry and more particularly to that of therapeutic chemistry.

A more particular subject of the invention is new compounds of quaternary ammonium type having at least one halogenoalkyl radical with a nitrogen.

Specifically a subject of the invention is new quaternary ammonium salts corresponding to general formula (I):

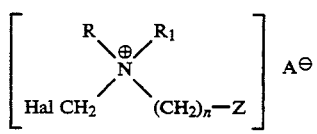

in which Hal is a halogen atom other than fluorine R and $R_1$, identical or different, are linear or branched chain lower alkyl radicals, n is an integer varying from 2 to 16, Z is an alkenyl radical having up to 3 carbon atoms, a carboxyl, or the $OR_2$ group where $R_2$ is a hydrogen, an optionally substituted lower alkyl radical, an acyl remainder derived from a saturated carboxylic or carbonic mineral or organic acid having 1 to 20 carbon atoms, a tocol radical, a sterol radical or a carboxamide chain with the following form:

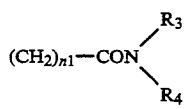

in which $n_1$ is an integer varying from 0 to 4, $R_3$ and $R_4$, identical or different, are either one a hydrogen and in this case the other substituent represents the alkylene chain of a heterocycle, optionally interrupted by one or more heteroatoms chosen from the group constituted by an oxygen or sulphur atom or the —NH— group, or identical or different lower alkyl radicals, or form together the alkylene chain of a nitrogenous heterocycle being able to contain another heteroatom as well as one or more functional groups chosen from the group constituted by a halogen, an oxo group, an amino group or a glucoside radical, and A is a hydroxyl or an anion of a mineral or organic acid with the restriction that the acyl remainder cannot include a 1-hydroxy 1,1-diphenyl acetic acid remainder, that when Hal is an iodine, $R_2$ is not an acetyl remainder and when Hal is a bromine and $R_2$ is an acetyl remainder, n is different from 2.

Among these, the following compounds are currently preferred:

the compounds of formula (IA):

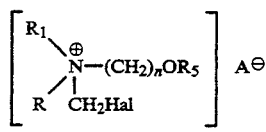

in which R, $R_1$ and Hal are as defined previously, n is and integer varying from 2 to 4, A is a hydroxyl or an anion of a mineral or organic acid, $R_5$ is a hydrogen, an acyl remainder derived from a mineral or organic acid having 1 to 18 carbon atoms or a lower alkyl optionally substituted by a hydroxy, a lower alkoxy, an amino group or an alkyl- or dialkylamino radical, the compounds of formula (IB):

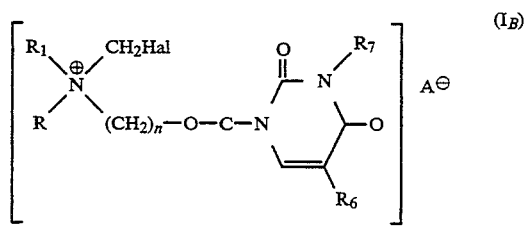

in which the substituents R, $R_1$, Hal, n and A are as defined previously, $R_6$ is a hydrogen, a halogen or a lower alkyl radical and $R_7$ is hydrogen or a sugar molecule, the compounds of formula (IC):

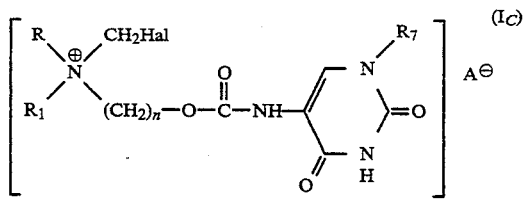

in which the substituents R, $R_1$, Hal, n, $R_7$ and A have the meanings given previously, the compounds of formula (ID):

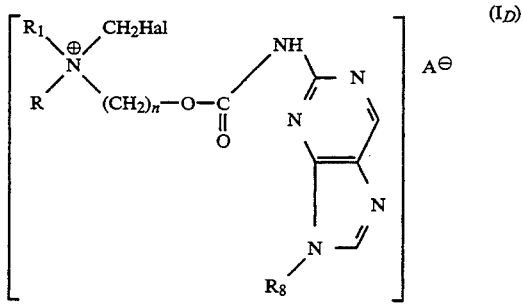

in which $R_1$, R, Hal and A are as defined previously $R_8$ is a hydrogen or a sugar molecule, the hydroxyls of which are free, blocked or phosphorylated, i.e. derivatives of guanine (2,9) or adenine (6,9), the compounds of formula (IE):

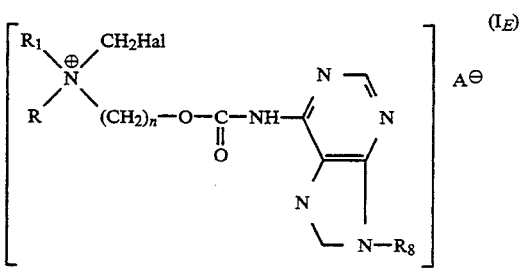

in which R, R₁, Hal, n, A and R₈ are as defined previously which are derivatives of cordycepin, the compounds of formula (IF):

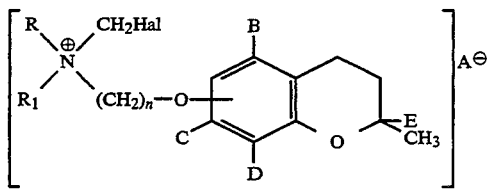

in which B, C and D are hydrogens, a hydroxyl or methyl radical and E is a farnesyl or phytyl chain and R, R₁, n, Hal and A retain the previous meanings i.e. ethers of α, β, γ or ε tocopherol,
the compounds of formula (I$_G$):

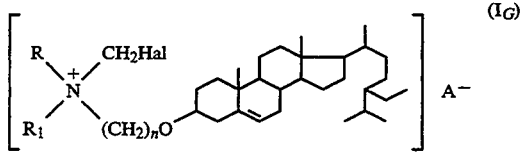

i.e. ethers of sitosterol in which R, R₁, Hal, n and A are as defined previously,
the compounds of general formula (IH):

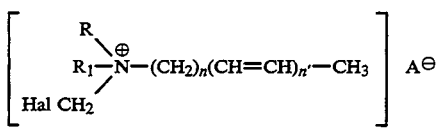

in which R, R₁, Hal and A are as defined previously n is an integer comprised between 6 and 16 n' is equal to 0 or 1,
the compounds of formula (Ii):

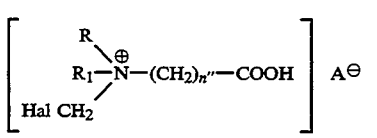

in which n" is equal to 1, 2 or 3 and R, R₁, Hal and A are as defined previously.

In the last two groups, there can be more particularly mentioned:

NN-dimethyl N-chloromethyl carboxymethyl ammonium chloride,

NN-dimethyl N-chloromethyl N-undecen-8-yl ammonium chloride,

NN-dimethyl N-chloromethyl N-ketyl ammonium chloride.

The invention also relates to pharmaceutical compositions containing as active ingredient at least one compound of general formula (I'):

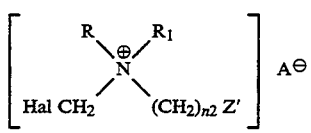

in which Hal, R and R₁ are as defined previously Z' is a hydrogen, the OR₂ group as defined previously, an alkenyl radical or a carboxyl group n is an integer varying from 1 to 16 and A is a hydroxyl or an anion of a therapeutically-compatible mineral or organic acid in combination or in a mixture with an excipient or an inert non-toxic pharmaceutically acceptable vehicle.

Among the compounds of formula (I'), the following can be mentioned more particularly: (chloromethyl)-trimethyl ammonium chloride or hydroxide intermediate synthesis compounds which are already known, but for which no therapeutic use had until now been described, as well as N-(chloromethyl) NN-dimethyl (beta-hydroxyethyl) ammonium salts, N-(chloromethyl) NN-dimethyl N(2,4-dioxo[1H]-pyrimidinyl) (carbonyloxy alkyl) ammonium salts, N-chloromethyl NN-dimethyl [(2,4-dioxopyrimidinyl) 5-amino carbonyl oxy alkyl)] ammonium salts and N-chloromethyl NN-dimethyl [(2,4-dioxo 5-fluoro[1H]pyrimidyl) carbonylalkyl] ammonium salts.

Among the said quaternary ammonium salts of general formula (I'), there can be more particularly mentioned the halides such as chlorides or bromides, sulphates, phosphates, nitrates, methane sulphonates, benzene sulphonates, naphthalene sulphonates, methylsulphates, acetates, benzoates or trimethoxybenzoates.

The pharmaceutical compositions according to the invention are presented in one of the appropriate forms for use by parenteral, digestive, rectal or percutaneous route. In addition to the active ingredient they contain a vehicle such as an aqueous medium, a glucose serum or a saline solution, or a solid excipient such as for example lactose, tricalcium phosphate, calcium sulphate, carboxymethyl cellulose, microcrystalline cellulose of colloidal silica. Binding agents can also be added to them such as polyvinyl pyrrolidone or methylcellulose, agents facilitating the wetting of the powder such as formolated casein, dispersing agents, surfactants, sweetening agents, flavouring and/or preserving or stabilizing agents. The average unit dose ranges from 0.1 to 50 mg according to the administration route. The quantities administered by parenteral route range from 0.1 to 10 mg per unit dose. The quantities administered by digestive or rectal route range from 5 to 25 mg. The quantities of active ingredient administered by percutaneous route range from 10 to 50 mg per unit dose.

The pharmaceutical compositions according to the invention have a use in human or animal therapeutics, in particular as anti-tumour agents. They are suitable in particular for the treatment of skin tumours either by themselves or in combination with standard chemotherapy. They also show immuno-suppressive properties which make them useful in the treatment of rheumatic illnesses and rheumatoid arthritis.

The invention also extends to a process for obtaining compounds of general formula (I) which consists of subjecting a dialkylamino alkanol of general formula (II):

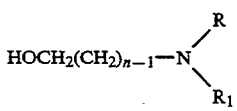
(II)

in which R, R₁ and n are as defined previously, to the action of a methylene halide in an inert solvent in order to form an NN-dialkyl N-(halomethyl) (hydroxyalkyl) ammonium salt of formula (III):

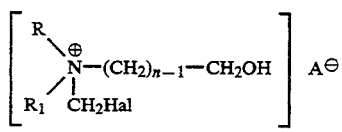
(III)

in which R, R₁, n and Hal are as defined previously and A⁻ is a halide then the latter is subjected either to the action of an esterification agent in order to form an ester of formula (IV):

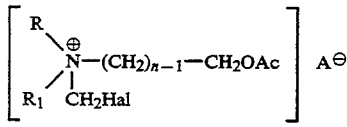
(IV)

in which Ac is the acyl remainder of a saturated mineral or organic acid and R, R₁, n, Hal and A are as defined previously, or to the action of an alkylation agent in order to form an ether of formula (V):

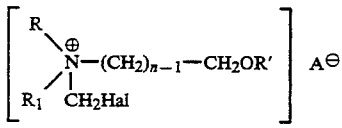
(V)

in which R' is a lower alkyl radical, optionally substituted by a hydroxyl or amine radical, or to the action of phosgene in order to form an intermediate chlorocarbonate which is reacted with a pyrimidine dione of general formula (VI):

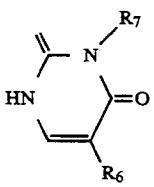
(VI)

in order to obtain the urethane of formula (I$_B$):

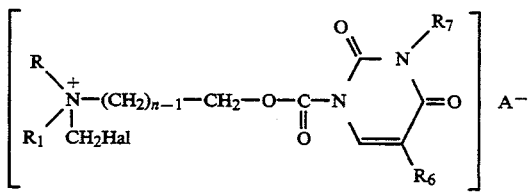
(I$_B$)

in which A, R, R₁, Hal, n, R₆ and R₇ have the previous meanings or with an amino pyrimidine dione of general formula (VIII):

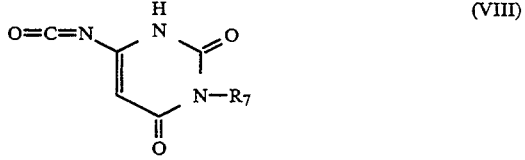
(VIII)

in order to obtain the urethane of formula (I$_C$):

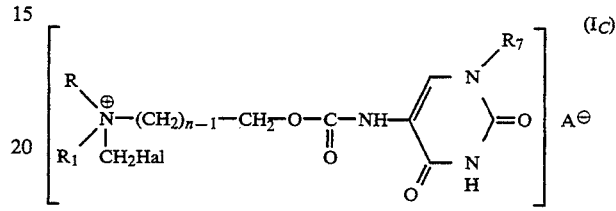
(I$_C$)

in which R, R₁, Hal, n, R₇ and A are defined as previously.

The quaternary ammonium salts of general formula (I) are easily converted into the hydroxide by the action of a basic agent such as an alkali, alkaline earth metal or silver hydroxide or carbonate or by passing them through an ion exchange resin in the alkaline form.

The hydroxides obtained in this way can, if desired, be converted again into another salt.

The invention also relates to a process for obtaining NN-dimethyl N-chloromethyl N-(carboxymethyl) ammonium chloride which consists of reacting monochloroacetic acid and dimethylamine in the presence of a proton acceptor to form NN-dimethylglycine which is subjected to the action of dichloromethane in a polar solvent, in order to form the desired quaternary ammonium salt.

Also a subject of the invention is a process for obtaining NN-dimethyl N-chloromethyl N-undecen-8-yl ammonium chloride in which an undecen-8-yl halide is reacted with dimethylamine then the tertiary amine formed in this way is condensed with dichloromethane in order to form the desired quaternary ammonium salt.

Also a subject of the invention is a process for obtaining NN-dimethyl N-chloromethyl N-ketyl ammonium chloride which consists of reacting NN-dimethyl hexadecylamine with dichloromethane in a polar solvent in order to obtain the desired quaternary ammonium salt.

Also the invention relates to an improved process for synthesizing NN-dimethyl N-chloromethyl (2-hydroxy ethyl) ammonium chloride which consists of subjecting NN-dimethyl ethanolamine to the action of dihydropyran in the presence of an organic acid in order to obtain the corresponding tetrahydropyranylated derivative which by reaction with dichloromethane gives NN-dimethyl N-chloromethyl N-(2-tetrahydropyranyl 2-oxy ethanol) ammonium chloride, the tetrahydropyranic ether of which is hydrolyzed by the action of a mineral acid and the desired quaternary ammonium salt is obtained.

The invention also relates to a variant of the process for obtaining the compounds of formula (I$_C$):

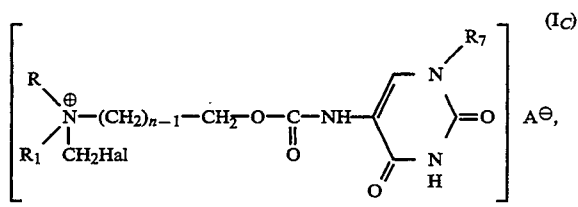

which consists of reacting an aminopyridine of formula (VIII):

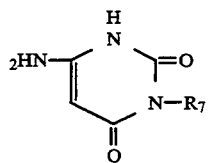

in which R₇ is defined as previously with phosgene in an inert solvent in order to form an isocyanate of formula (IX):

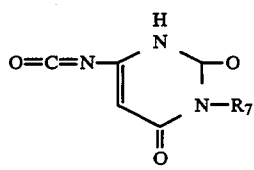

in which R₇ is as defined previously which is not purified and is directly condensed with a compound of formula (III) in order to obtain the desired compound of formula (I$_C$):

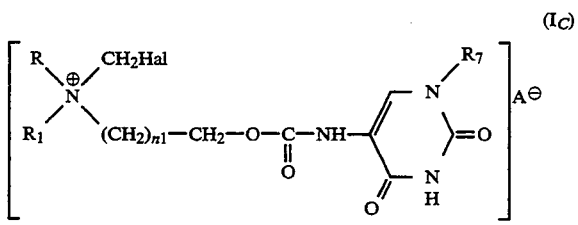

in which the radicals R, R₁, Hal, n₁ and R₇ retain their previous meanings A is an anion derived from a mineral or organic acid which, if desired, can be converted into the corresponding ammonium hydroxide by the action of a basic agent.

Also, a subject of the invention is a variant of the process in which a pyrimidine dione of formula (VI):

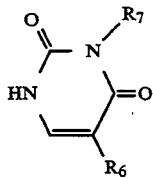

in which R₆ and R₇ are defined as previously is subjected to the action of phosgene in an inert solvent then heated to above 100° C. in order to form an isocyanate of general formula (VII):

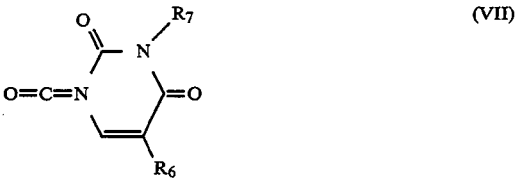

in which R₆ and R₇ have the meanings given previously which is not purified and is condensed as it is with an NN-dialkyl N-(halomethyl) N-(hydroxyalkyl) ammonium salt of formula (III):

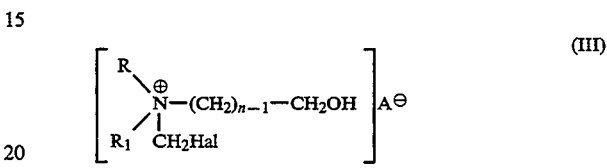

in which R, R₁ Hal, n and A are defined as previously, in order to form a urethane of general formula (I$_B$):

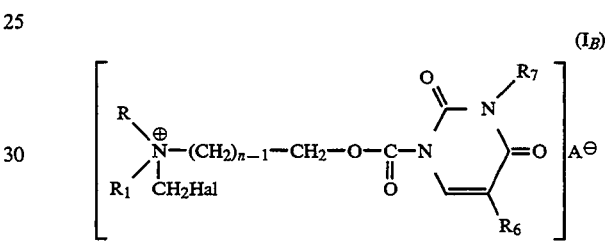

in which the substituents R, R₁, Hal, n, R₆ and R₇ retain their previous meanings and A is an anion derived from a mineral or organic acid which can be converted into the hydroxide by the action of a basic agent.

The invention also relates to a variant of the process for obtaining the compounds of formula (I$_C$) in which the compounds of formula (I$_C$) are prepared according to a process which consists of reacting an aminopyrimidine of formula (VIII):

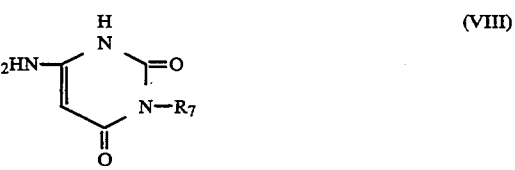

in which R₇ is defined as previously with phosgene in an inert solvent in order to form an isocyanate of formula (IX):

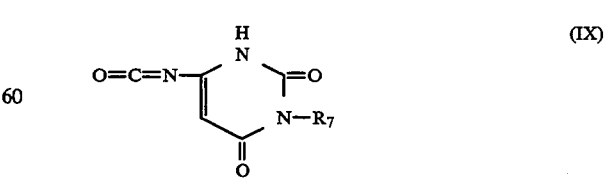

in which R₇ is defined as previously which is not purified and is condensed directly with a compound of formula (III) in order to obtain the desired compound of formula (I$_C$):

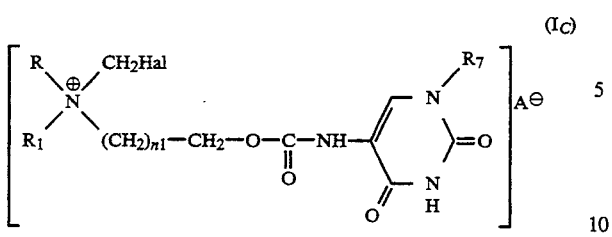

in which the radicals R, $R_1$, Hal, $n_f$ and $R_7$ retain their previous meanings A is an anion derived from a mineral or organic acid which can, if desired, be converted into the corresponding ammonium hydroxide by the action of a basic agent.

The following examples illustrate the invention without however limiting it:

EXAMPLE I

NN-DIMETHYL N-CHLOROMETHYL N-CARBOXY METHYL AMMONIUM CHLORIDE

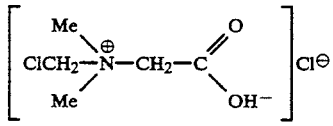

30 g of monochloracetic acid and 27 g of sodium bicarbonate are put in solution in 100 ml of absolute ethanol. 203 ml of dimethylamine (40% solution) is added at 0° C. The mixture is agitated for 12 hours at 20° C., concentrated to dryness under vacuum. The pH is adjusted to 14 with soda then filtration and evaporation are carried out.

The product obtained is put in solution in 70 ml of isopropyl alcohol, 70 ml of acetonitrile, 56 ml of water and 300 ml of methylene chloride. The resultant medium is treated under reflux for 16 hours.

After concentrating to dryness under vacuum, the residue is then put in solution in n-butanol. Filtration is carried out followed by crystallization from an ethanol-/isopropyl ether mixture.

36.3 g of quaternary ammonium chloride is collected.

ELEMENTARY ANALYSIS

C=32; H=5.85; Cl=37.76; N=7.44; O=17.02% IR Spectrum (KBr) $\omega$ cm$^{-1}$: 800, 975, 1481, 1633, 3045, 3428. NMR ($^1$H): (CD$_3$OD) internal reference TMS; $\delta$ in ppm:

3.3 (S, 6H—N$^+$(CH$_3$)$_2$

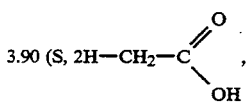

(S, 2H, N—CH$_2$Cl)

Mass Spectrum: M: 188

EXAMPLE II

NN-DIMETHYL N-CHLOROMETHYL N-UNDECEN-8-YL AMMONIUM CHLORIDE

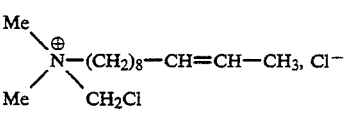

STAGE I: Dimethyl (undecen-8-yl) amine

A mixture of 96.49 g of undecylenyl bromide and 314.0 ml of dimethylamine is agitated for 48 hours at 20° C. At the end of the reaction, the pH is brought to 2 by a hydrochloric acid solution (10%). The amine is extracted with methylene chloride.

The organic phase is evaporated under vacuum. The pH is adjusted to 14 by a soda solution (30%). The residue is taken up in n-butanol, filtered on celite, brought to dryness.

STAGE II: NN-dimethyl N-chloromethyl N-(undecen-8-yl) amine chloride

The amine obtained in Stage I is treated under reflux for 48 hours in 5 volumes of methylene chloride. The reaction is monitored by TLC in an ethyl acetate/methanol/acetic acid (50/25/25) system and indicated with DRAGENDORFF reagent. After concentration under vacuum, the residue is dissolved in n-butanol, filtered on celite then concentrated under vacuum. After drying, 40 g of product is obtained which is in the form of a dark brown oil.

ELEMENTARY ANALYSIS

C=68.16; H=11.8; Cl=14.40; N=5.68% IR Spectrum (NaCl) $\omega$ cm$^{-1}$: 799, 992, 1464, 1653, 2855, 2925 NMR $^1$H {CD$_3$OD }; internal reference: TMS; $\delta$ in ppm:

1.1–1.4 (SNR, 12H, (CH$_2$)$_6$—)

1.6–1.8 (SNR, 5-H, CH$_3$ and CH$_2$)

3.3 (S, 6H, N (CH$_3$)$_2$), 3.5 (T, 2H, —(CH$_2$)—N)
4.9 (wide signal, 2H, ethylenic)
5.4 (S, 2H, N—CH$_2$ Cl)

EXAMPLE III

NN-DIMETHYL N-CHLOROMETHYL N-CETYL AMMONIUM CHLORIDE

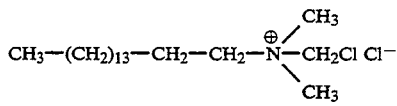

A mixture of 31.5 g of NN-dimethyl N-hexadecyl amine, 40.0 ml of isopropyl alcohol, 30.0 ml of acetonitrile, 25.0 ml of distilled water and 100.0 ml of methylene chloride is heated under reflux for 48 hours.

At the end of the reaction, the mixture is concentrated to dryness under vacuum and recrystallized from isopropyl ether, the resultant product is separated, washed with acetone then with hexane. Drying is carried out under vacuum at ambient temperature to a constant weight. 19.2 g of white crystals is obtained. Yield 61%. Melting point: 99.9° C.

| Centesimal analysis: | C | H | Cl | N | in % |
|---|---|---|---|---|---|
| calculated: | 64.4 | 11.6 | 20.05 | 3.95 | |
| found: | 64.32 | 11.74 | 19.03 | 3.95 | |

IR Spectrum (KBr) $\omega$ cm$^{-1}$: 797, 969, 1472, 3014
NMR $^1$H (CD$_3$OD); internal reference TMS; $\delta$ in ppm:
0.9 (t, 3H, H=7 Hz, CH$_3$—)
1.2–1.5 (SNR, 26H, (CH$_2$)$_{13}$)
1.8 (m.n.R, 2H, C$\underline{H}_2$—CH$_2$N$^+$)
3.2 (S, 6H, N$^+$($\overline{CH_3}$)$_2$)
3.45 (dr, 2H, H=5 Hz, —(CH$_2$)—N$^+$)
5.30 ( S, 2H, —CH$_2$Cl)

EXAMPLE IV
(N-CHLOROMETHYL)-NN-DIMETHYLAMMONIO-2 ETHANOL CHLORIDE

STAGE A: Preparation of N,N-dimethylamino-2-(tetrahydro-2-pyranyloxy) ethanol 10.0 mg of paratoluenesulphonic acid, 8.7 ml of dihydropyran, then 7.12 g of N,N-dimethylethanol-amine are mixed together at 20° C. The temperature is taken to 60° C., and after agitation for 2 hours the mixture is returned to 20° C. 0.5 g of sodium bicarbonate is then added. Agitation is continued for one hour. The tetrahydropyranyloxylated derivative is obtained which is immediately reacted.

STAGE B: (N-chloromethyl) N,N-dimethyl-2 (tetrahydro-2-pyranyloxy)-ethyl ammonium chloride 0.08 mole of the previous crude product, 10.0 ml of isopropanol, 10.0 ml of acetonitrile, 10.0 ml of methylene chloride and 8.0 ml of distilled water are heated under reflux for 5 hours in a 100 ml Erlenmeyer flask with magnetic agitation. Concentration is carried out under vacuum. The residue is then converted into a hydroxylated compound by hydrolysis of the ether function.

STAGE C: (N-chloromethyl) N,N-dimethylammonio-2 ethanol chloride

The previous crude product is put in solution in 0.5 vol. of a 0.6% hydrochloric acid solution and 0.5 vol. of ethanol. The mixture is taken to 50° C. for 45 minutes, then neutralized with sodium carbonate, followed by filtration on celite. After concentration under vacuum, the product is crystallized from isopropyl alcohol. The purity of the product obtained is greater than that of the product described in Example III.

EXAMPLE V
SYNTHESIS OF (CHLOROMETHYL)-TRIMETHYLAMMONIUM CHLORIDE

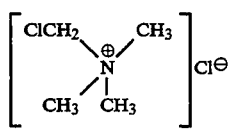

The following are mixed together in a 1000 ml Erlenmeyer flask with magnetic agitation:
50 ml of methylene chloride
60 ml of isopropanol
60 ml of acetonitrile
180 ml of triethylamine in 30% aqueous solution The Erlenmeyer flask is sealed with a ground glass stopper and left under agitation at ambient temperature for 5 days. After concentrating to dryness under vacuum, the residue is taken up three times in 250 ml of absolute ethanol, concentrating under vacuum each time.

The residue is recrystallized from a 3/1 mixture of ethyl acetate/absolute ethanol.

68 g of a very hygroscopic, clear grey powdered product is obtained. Yield 40.3%,

| ANALYSIS BY WEIGHT IN %: | | | | |
|---|---|---|---|---|
| C | H | N | O | Cl |
| 33.09 | 7.72 | 9.58 | 2.68 | 46.62 |

Infrared (film): $\omega$ cm$^{-1}$: 797, 968, 1400, 1476, 3018
NMR $^{13}$C (D$_2$O; internal reference TMS: $\delta$in ppm):
52.7 (CH$_3$+N)
71.7 (CH$_2$—Cl)
Mass spectrum: M$^+$(144)

EXAMPLE VI
TRIMETHYL (CHLOROMETHYL) AMMONIUM HYDROXIDE

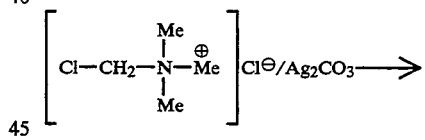

0.5 g of (chloromethyl)-trimethylammonium chloride (MW=144, or 0.0035 mole) is dissolved in 20 ml of 95% ethanol at 20° C. 1 g of silver carbonate (MW=275.77), or 0.0036 mole in suspension in 10 ml of demineralized water is added to this solution.

The silver chloride is eliminated by filtration; the filtrate is concentrated under vacuum, and kept as it is until used. The reaction is quantitative.

IR Spectrum (NaCl) $\omega$ cm$^{-1}$: 798, 972, 1453, 1469
NMR $^1$H (DMSO d6, internal reference TMS, $\delta$ in ppm):
3.18 (5, 9H) $^+$N (CH$_3$)$_3$
5.5 (5, 2H, CH$_2$ Cl)

EXAMPLE VII

PREPARATION OF (N-CHLOROMETHYL)-N,N-DIMETHYL AMMONIO-2-ETHANOL CHLORIDE

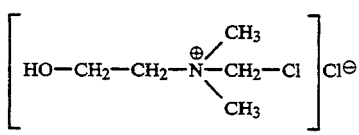

The following are heated under reflux for 5 days in a 2 liter Erlenmeyer flask with magnetic agitation:
150 ml of dimethylamino ethanol
180 ml of isopropanol
180 m of acetonitrile
180 ml of methylene chloride
150 ml of distilled water Concentration is carried out under vacuum. The residue is triturated three times with hexane and isopropyl ether. The product is crystallized from isopropyl ether.

100 g of a very hygroscopic powdered product is obtained. Yield 37%.

ANALYSIS BY WEIGHT IN %:

IR Spectrum (film): $\omega$ cm$^{-1}$: 857, 919, 958, 1086, 1479, 3015, 3265

NMR [$^1$H] (CD$_3$OD, internal reference TMS, $\delta$ in ppm):
3.3 (5, 6H N (CH$_3$)$_2$)
3.65 (triplet, 2H, CH$_2$N$^+$)
4.05 (triplet, 2H, J-5 Hz CH$_2$O)
5.40 (S, 2H, N CH$_2$ Cl)
Mass spectrum: M=174.

EXAMPLE VIII

PREPARATION OF 3-[(2-CHLOROMETHYL)DIMETHYLAMMONIO) ETHOXYCARBONYL]-2,4-(1H) DIOXOPYRIMIDINE CHLORIDE

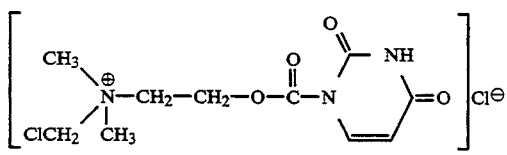

The following is introduced into a 2 liter Erlenmeyer flask:
105 ml of phosgene (20% solution in toluene) which is cooled down to a temperature of 4/5° C.
A mixture constituted by:
32 g of N-chloromethyl N,N-dimethylammonio-2-ethanol chloride
30 ml of triethylamine
200 ml of toluene
is then added over 30 minutes and under magnetic agitation.

The mixture is left for one hour under agitation at a low temperature (4/5° C.), the temperature is then taken to 20° C. and the following are added:
22.5 g of uracil
30 ml of triethylamine
200 ml of toluene.

Agitation is maintained at 20° C. for 15 hours; the end of the reaction is monitored by chromatography on silica gel in a CHCl$_3$/MeOH/NH$_4$OH (85:15:1.5) system. Indicated with DRAGENDORFF reagent.

The reaction product is cooled down to −15° C. (pH about 14). Filtration is carried out through a Buchner filter funnel and flask. The crystals are washed with essence B. Finally, the product is purified by percolation on a neutral alumina column (MERCK, 1077) with methylene chloride as initial eluant. The product is eluted with acetone.

After purification and drying under vacuum, 15 g of product is obtained, that being a yield of 28%.

EXAMPLE IX

PREPARATION OF 5-[2-(CHLOROMETHYL)DIMETHYLAMINO ETHOXYCARBAMYL]-2,4-DIOXO (1H, 3H) PYRIMIDINE CHLORIDE

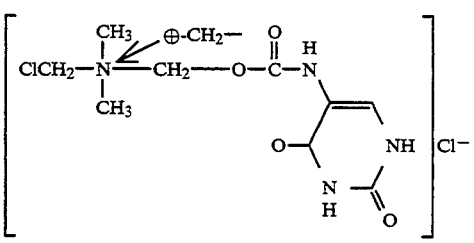

The following are introduced into an Erlenmeyer flask:
30 g (0.24 mole) of 5-aminouracil
300 ml of toluene The mixture is brought to 0° C., then the following is added:
342 ml of phosgene at 20% in toluene.

The mixture is treated under reflux for one hour. The temperature is then taken to 80° C.; the vacuum is established, then the temperature is taken to 110° C. for 15 minutes. The temperature is then lowered to −15° C. The crystals formed are filtered through a Buchner filter funnel and flask, washed with toluene, then with essence B.

28 g of intermediate isocyanate is obtained which is not purified.

The crude isocyanate (18 g) prepared previously is put in solution in 100 ml of xylene, 18.10 g of N-chloromethyl N,N-dimethylamino 2-ethanol chloride is added.

The mixture is agitated for half an hour at 20° C. The end of the reaction is monitored by chromatography on a thin layer of silica gel. The chromatogram is developed in a CHCl$_3$/MeOH/NH$_4$OH (85/15/1.5) system; indicated with DRAGENDORFF reagent.

The product is purified by passing through a column of silica gel. The elutions are carried out with essence B progressively enriched with ethyl acetate.

In this way 17 g of product is obtained, that being a yield of 50%.

The structure of the product and its molecular weight were confirmed by elementary analysis, NMR [$^1$H] and mass spectrum. These compounds can be used as anti-neoplastic agents and also as immuno-depressants.

I claim:
1. N,N-dimethyl-N-chloromethyl-N-cetyl-8-yl-quaternary ammonium chloride.
2. An antitumor composition comprising an antitumorally effective amount of a compound of claim 1 and an inert pharmaceutical carrier.
3. A method of treating tumors in warm-blooded animals comprising administering to warm-blooded animals an antitumorally effective amount of a compound to claim 1.

* * * * *

UNITED STATES PATENT AND TRADEMARK OFFICE
CERTIFICATE OF CORRECTION

PATENT NO. : 5,399,590

DATED : March 21, 1995

INVENTOR(S) : JEAN M. GASTAUD

It is certified that error appears in the above-identified patent and that said Letters Patent is hereby corrected as shown below:

On the title page:

[76]   Change "Domaine Bellecombe, 74930 Reignier, France"

to read   --Le Victoria
             13, Boulevard Princesse Charlotte
             98000 Monaco (Principaute de Monaco)--

Signed and Sealed this

Third Day of October, 1995

Attest:

BRUCE LEHMAN

Attesting Officer        Commissioner of Patents and Trademarks